United States Patent [19]

Stephens et al.

[11] Patent Number: 4,857,330
[45] Date of Patent: Aug. 15, 1989

[54] CHLORPHENIRAMINE THERAPY

[75] Inventors: Sally I. Stephens, Mountain View; Lawrence G. Hamel; Glen E. Barclay, both of Sunnyvale; Patrick S. L. Wong, Hayward, all of Calif.

[73] Assignee: Alza Corporation, Palo Alto, Calif.

[21] Appl. No.: 176,561

[22] Filed: Apr. 1, 1988

Related U.S. Application Data

[63] Continuation of Ser. No. 853,109, Apr. 17, 1986, abandoned.

[51] Int. Cl.⁴ .............................................. A61M 31/00
[52] U.S. Cl. .................................... 424/424; 424/468; 424/471
[58] Field of Search ............................. 424/422–426, 424/468–473

[56] References Cited

U.S. PATENT DOCUMENTS

| 4,014,334 | 3/1977 | Theeuwes et al. | 604/294 |
|---|---|---|---|
| 4,116,241 | 9/1978 | Theeuwes et al. | 604/892 |
| 4,167,558 | 9/1979 | Sheth et al. | 424/19 |
| 4,405,597 | 9/1983 | Takagishi et al. | 424/35 |
| 4,439,194 | 3/1984 | Harwood et al. | 604/890 |
| 4,439,195 | 3/1984 | Swanson et al. | 604/890 |
| 4,522,625 | 6/1985 | Edgren | 604/890 |
| 4,576,604 | 3/1986 | Guittard et al. | 604/890 |
| 4,631,284 | 2/1986 | Salpeker et al. | 514/277 |

Primary Examiner—Nancy A. B. Swisher
Attorney, Agent, or Firm—Paul L. Sabatine; Edward l. Mandell; Steven F. Stone

[57] ABSTRACT

An osmotic dosage form is disclosed for delivering chlorpheniramine.

9 Claims, 1 Drawing Sheet

CHLORPHENIRAMINE THERAPY

CROSS-REFERENCE TO RELATED APPLICATIONS

This application is a continuation of U. S. Pat. Application Ser. No. 06/853,109 filed Apr. 17, 1986 now abandoned, which application is incorporated herein by reference and benefit is claimed of its filing date. These applications are assigned to ALZA Corporation of Palo Alto, Calif.

FIELD OF THE INVENTION

This invention pertains to chlorpheniramine therapy. More particularly, the invention related to a dosage form for delivering chlorpheniramine at a therapeutically effective rate over a prolonged period of time.

BACKGROUND OF THE INVENTION

Chlorpheniramine is a potent, short-acting antihistamine. Chlorpheniramine's antihistamine pharmacodynamic action substantially diminishes or abolished the action of histamine in the body. Chlorpheniramine achieves these results by occupying the receptor sites, mainly the H-1 receptor sites, in the effector cells to the exclusion of histamine. The antihistamine chlorpheniramine is thus an H-1 receptor antagonists.

Chlorpheniramine is indicated therapeutically for the palliative treatment of allergic reactions. Chlorpheniramine is indicated for the relief of asthma, for the relief of symptoms of seasonal hay fever, for nasal irritation and discharge, for the management of uticaria, skin irritations, pruritus ani, contact dermatitis, insect bites, and the like.

The prior art administered chlorpheniramine orally because chlorpheniramine is well-absorbed following oral administration. A common fault with the prior art dosage forms used for oral administration is that they do not deliver chlorpheniramine at a rate controlled by the dosage form. For example, chlorpheniramine is released from one prior art dosage form by leaching from minute pellets coated with complex digestible substances, at a rate dependent on the volume of fluid present in the environment of use. This kind of release is not rate controlled by a dosage form.

In the light of the above presentation, it will be appreciated by those versed in the dispensing art that a pressing need exists for a novel dosage form that can deliver chlorpheniramine at a rate controlled by the dosage form. The need exists also for a dosage form that can deliver chlorpheniramine for obtaining its beneficial effects over a prolonged period of time.

OBJECT OF THE INVENTION

Accordingly, it is an immediate object of this invention to provide a dosage form for the controlled delivery of chlorpheniramine for its therapeutic effects, and which dosage form overcomes the shortcomings known to the prior art.

Another object of this invention is to provide a novel dosage form that can deliver chlorpheniramine at a slow and continuous rate of at least ten hours, thereby providing an improvement and advancement for dispensing chlorpheniramine.

Another object of this invention is to provide a novel dosage form for delivering chlorpheniramine at a rate essentially-free of dose-breakthrough, by delivering chlorpheniramine at a substantially even maintenance rate of therapy, thereby providing a prolonged and optimal level of chlorpheniramine therapy.

Another object of the invention is to provide a dosage form for dispensing chlorpheniramine, which dosage form provides convenience of oral chlorpheniramine administration accompanied by a smoother chlorpheniramine delivery instead of the high and low points of delivery of the currently available dosage forms.

Another object of the invention is to provide a dosage form for dispensing the antihistamine chlorpheniramine for its resultant therapeutic effect adapted and designed to provide at least ten hours of sustained release antihistamine chlorpheniramine medication following the administration of a single, oral dosage form.

Another object of the invention is to provide a novel dosage form manufactured as an oral, osmotic delivery device that incorporates controlled and sustained release dispensing of chlorpheniramine over a prolonged period of time, thereby substantially overcoming the short duration of action associated with chlorpheniramine.

Another object of the invention is to provide a novel dosage form for dispensing chlorpheniramine first from an exterior lamina comprising chlorpheniramine and secondly from a compartment comprising chlorpheniramine, thereby providing a pharmaceutical program of chlorpheniramine administration to a recipient.

Other objects, features and advantages of the invention will be more apparent to those versed in the chlorpheniramine art from the following specification, taken in conjunction with the drawing figures and accompanying claims.

BRIEF DESCRIPTION OF THE DRAWINGS

In the drawing figures, which are not drawn to scale, but are set forth to illustrate various embodiments of the invention, the drawing figured are as follows.

In the drawing figures and in the specification, like parts in related figures are identified by like numbers. The terms appearing earlier in the specification, and in the description of the drawing figures, as well as embodiments thereof, are further described elsewhere in the disclosure.

DETAILED DESCRIPTION OF THE DRAWING FIGURES

Figure 1:
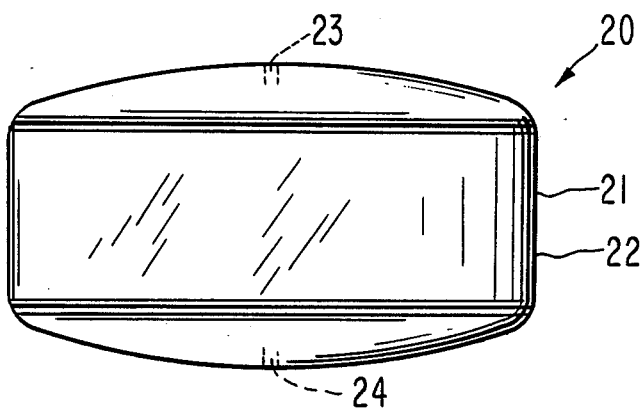
FIG. 1 is a side view of a dosage form designed and shaped for orally administering chlorpheniramine to the gastrointestinal tract of a warm-blooded animal.

Turning now to the drawing figures in detail, which drawing figures are an example of the dosage forms provided by the invention, and which examples are not to be construed as limiting, one example of the dosage form is illustrated in FIG. 1 and it is designated by the numeral 20. In FIG. 1, dosage form 20 comprises a body member 21 comprising a wall that surrounds and forms an internal compartment, not seen in FIG. 1. Dosage form 20 further comprises at least one exit means 23, or more than one exit means 24 for connecting the interior of dosage form 20 with the exterior environment of use.

Figure 2:
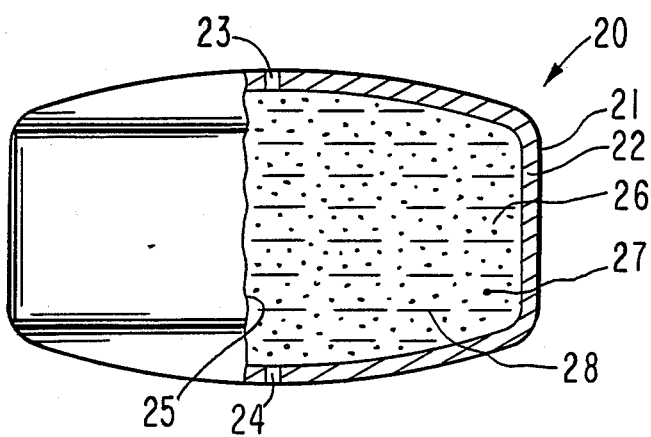
FIG. 2 is an opened view of the dosage form of FIG. 1 for illustrating the structure of the dosage form.

FIG. 2 is a view of dosage form 20 of FIG. 1 seen in opened section with wall 22 cut-away at 25 for illustrating the internal structure of dosage form 20. In FIG. 2, dosage form 20 comprises body member 21, wall 22 that surrounds and defines internal compartment 26, exit means 23 and exit means 24 for connecting compartment 26 with the exterior of dosage form 20.

Wall 22 of dosage form 20 comprises in at least a part a composition that is permeable to the passage of an exterior fluid present in the environment of use and substantially impermeable to the passage of chlorpheniramine. Wall 22 of dosage form 20 is substantially inert, and it maintains its physical and chemical integrity during the chlorpheniramine dispensing life of dosage form 20. The phrase "keeps its physical and chemical integrity" means wall 22 does not lose its structure and it does not change during the dispensing life of dosage form 20. Wall 22 in a presently preferred embodiment is formed of a composition comprising cellulose triacetate and hydroxypropyl cellulose. The wall-forming composition comprises from 70 to 85 weight percent cellulose triacetate and from 15 to 30 weight percent hyroxypropyl cellulose, with the total weight percent equal to 100 Wall 22 in one presently preferred manufacture comprises 75 weight percent cellulose triacetate and 25 weight percent hydroxypropylcellulose. In another preferred embodiment, wall 22 comprises 80 weight percent cellulose triacetate and 20 weight percent hydroxypropylcellulose. The acetyl content of the cellulose triacetate can be from 39.8% to about 43.5%. Wall 22 in operation in a fluid environment of use exhibits an increased permeability to the passage of fluid over time due to the fluid hydration of the hydroxypropyl cellulose present in wall 22. This unique property of wall 22 acting in cooperation with dosage form 20, enables the dosage form to deliver greater than 90 to 95% of its chlorpheniramine over a prolonged period of at least 12 hours or longer.

Internal compartment 26 houses a dispensable therapeutic composition comprising the beneficial drug chlorpheniramine 27, identified by dots, and other composition forming members 28 comprising mannitol, poly(vinylpyrrolidone), magnesium stearate, stearic acid and microcrystalline cellulose, identified by dashes. The drug chlorpheniramine 27 is present in a presently preferred embodiment as the pharmaceutically acceptable maleate. Chlorpheniramine maleate exhibits a solubility of 514 mg/ml at 37° C. The osmotic pressure of a saturated solution of chlorpheniramine maleate at 37° C. is 11.3 atmospheres, atm, as measured by vapor pressure osmometry. These properties of chlorpheniramine maleate, its low osmotic pressure and its high solubility in aqueous including biological fluids are unacceptable for delivering chlorpheniramine from an osmotic dosage form. That is, these properties do not lend themselves to osmotic-controlled delivery because chlorpheniramine maleate is released too quickly in a period of less than 8 hours and it is released also in a declining rate of release. The present invention sought to improve the delivery properties of chlorpheniramine maleate by formulating chlorpheniramine maleate with sorbitol as a chlorpheniramine dispensing adjunct. Unfortunately, the dosage form comprising both chlorpheniramine maleate and sorbitol exhibited an unacceptable release pattern. The dosage form comprising sorbitol released over 50% of the drug chlorpheniramine maleate between the sixth and tenth hours. In artificial gastric fluid, the dosage form had an average rate of release of 0.89 mg/hr and in artificial intestinal fluid the dosage form had an average rate of release of 2.53 mg/hr during the same time span. Now, the present invention has unexpectedly discovered that structurally similar mannitol can be used successfully as a dispensing adjunct for chlorpheniramine. A dosage form comprising chlorpheniramine maleate and mannitol delivered chlorpheniramine at a controlled rate over a prolonged period of greater than 16 hrs, and during a corresponding time span in artificial gastric fluid the dosage form exhibited an average rate of release of 1.0 mg/hr, and in artificial intestinal fluid the dosage form had an average rate of release for chlorpheniramine maleate of 1.01 mg/hr. This invention further enhances both the operability and the effectiveness of the dosage form by maintaining a mannitol concentration of from 1.5 to 6 times greater than the concentration of chlorpheniramine in the osmotic dosage form.

The amount of chlorpheniramine present in compartment 26 of osmotic dosage form 20 is from 2 mg to 24 mg of a member selected from the group consisting of chlorpheniramine and its pharmaceutically acceptable addition salts; from 35 mg to 100 mg of mannitol, from 0 to 5 mg of poly/vinylpyrrolidone, from 0 to 5 mg of magnesium stearate, from 0 to 5 mg of stearic acid and from 0 to 20 mg of microcrystalline cellulose. In a more presently preferred manufacture compartment 26 comprises 46 to 8 mg of chlorpheniramine maleate, 40 to 50 mg of mannitol, 1 to 3 mg of poly(vinylpyrrolidone) and 0.2 to 2 mg of magnesium stearate; in another presently preferred manufacture compartment 26 comprises 10 to 15 mg of chlorpheniramine, 45 to 75 mg of mannitol, 1 to 4 mg of poly(vinylpyrrolidone) and 0.3 to 2 mg of magnesium stearate. In either of the preferred embodiments compartment 26 may additionally contain 4.5 to 9 mg of microcrystalline cellulose, or the like.

Figure 3:
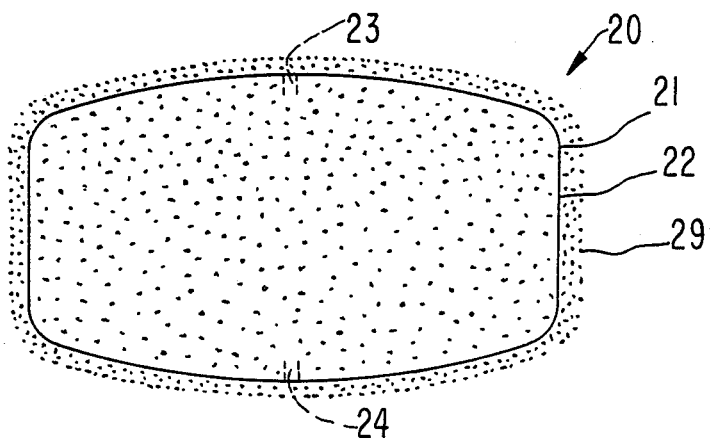
FIG. 3 is a side view of a dosage form comprising a dosage amount of chlorpheniramine on its exterior surface for administering chlorpheniramine instantly and in a short period of time to a recipient; and, FIG. 4 is an opened view of the dosage form of FIG. 3 manufactured as an osmotic delivery device for administering chlorpheniramine instantly and in a short time span from the exterior of the dosage form followed by administering chlorpheniramine from the interior of the dosage form over a prolonged period of time.

FIG. 3 illustrates another dosage form 20 provided by the invention. Dosage form 20 makes available an instant delivery of chlorpheniramine. Dosage form 20 of FIG. 4 comprises an exterior chlorpheniramine drug coat 29 that surrounds in at least a part exterior wall 22 of body 21 of dosage form 20. Exterior chlorpheniramine coat 29 compares a pharmaceutically acceptable carrier hydroxypropylcellulose suitable for releasably coating chlorpheniramine to the exterior wall 22 of dosage form 20. The amount of chlorpheniramine in the exterior coat generally from 1 mg to 15 mg and the amount of hydroxypropylcellulose is form 0.5 to 10 mg. The instant chlorpheniraminehydroxypropylcellulose coat releases chlorpheniramine to a biological fluid environment of use instantly and over a 30 minute chlorpheniramine delivery period.

Figure 4:
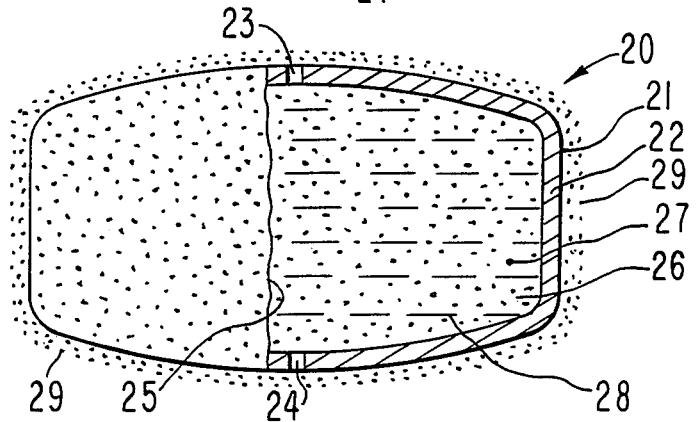

FIG. 4 illustrates another dosage form 20 provided by the invention. In FIG. 4, dosage form 20 administers chlorpheniramine from exterior coat 29 and it delivers chlorpheniramine from interior compartment 26. Dosage form 20 comprises body 21, wall 22, compartment 26, chlorpheniramine 27, mannitol and composition form-members 28, exterior coat 29 comprising chlorpheniramine, and exit means 23 and 24.

The expression "exit means" as used herein comprises means and methods suitable for releasing chlorpheniramine 27 from compartment 26 through at least one exit means 23 and 24. The expression includes at least one passageway or orifice that passes through wall 22 for communicating with compartment 26. The expression "at least one" includes passageway, aperture, bore, porous element through which a drug can pass, a hollow fiber, capillary, tube and the like. The expression includes a material that erodes or is leached form wall 22 in the fluid environment of use to produce at least one passageway in dosage form 20. Representative materials suitable for forming at least one exit passageway, or a multiplicity of passageways include an erodible poly(glycolic) or poly(lactic) acid member in the wall, a gelatinous filament, leachable materials such as fluid removable pore forming salts, oxides, polysaccharides, or the like. A passageway or a plurality of passageways can be formed by leaching a material such as sorbitol from the wall to provide a controlled release pore-passageway. The passageway can have any shape such as round, triangular, square, elliptical, and the like. The dosage form can be constructed with one or more passageways in spaced apart relation on more than a single surface of the dosage form. Passageways and equipment for forming passageways are disclosed in U.S. Pat. Nos. 3,916,899; 4,063,064; and 4,088,864. Pore-passageways of controlled dimensions formed by leaching are disclosed in U.S. Pat. No. 4,200,098.

The wall of the osmotic dosage form, and the exterior coat, can be formed in one technique using the air suspension procedure. This procedure consists in suspending and tumbling the chlorpheniramine and other compartment forming members previously pressed into a unit mass in a current of air and a wall forming, or an outer coat forming composition, until in either operation the wall, or the outer coat is applied to the pressed composition. The air suspension procedure is well suited for independently forming the wall or the coat. The air suspension procedure is described in U.S. Pat. No. 2,799,241; in *J. Am. Pharm. Assoc.*,Vol. 48, pp. 451 to 459, 1959; and, ibid, Vol. 49, pp. 82 to 84, 1960. The osmotic dosage form can be coated with a wall, or outer-most coat with the wall forming, or coat forming composition, with a Wurster ® air suspension coater, using for example methylene dichloride-methanol cosolvent. The Aeromatic ® air suspension coater can be used also employing a cosolvent. Other wall or coat applying techniques such as pan coating can be used for providing the dosage form. In the pan coating system, the wall or coat forming composition, are deposited by successive spraying of the composition by tumbling in a rotating pan. A pan coater is used to produce a thicker wall or coat. A larger volume of solvent, such as methanol can be used in a cosolvent to produce a thinner wall or coat. Finally, the wall or the coated compartments are dried in a forced air oven at 50° C. for a week to free the dosage form of solvent. Generally, the wall formed by these techniques have a thickness of 2 to 20 mils with a presently preferred thickness of 4 to 10 mils. THe exterior coat chlorpheniramine dose generally will be a thickness of 0.5 to 15 mils, usually 0.5 to 6 mils.

Exemplary solvents suitable for manufacturing the wall or the outer coat include inert inorganic or organic solvents that do not adversely harm the wall, the coat, or the final system. The solvents broadly include a member selected from the group consisting of an alcohol, ketone, ester, ether, aliphatic, hydrocarbon, halogenated, cycloaliphatic, aromatic, heterocyclic, aqueous, and the like.

The osmotic dosage form of the invention is manufactured by standard manufacturing techniques. For example, the compartment forming ingredients are formulated by wet granulation using an organic solvent, or cosolvent as the granulating fluid. The ingredients forming the compartment in one manufacture are individually passed through a 40 mesh screen and then thoroughly blended in a mixer. Next, a binder is dissolved in a portion of the granulation fluid and this solution is sprayed onto the dry powder with continuous mixing in the granulator column. Next, the wet blend is forced through a 20 mesh screen onto oven trays and dried for 18 to 24 hrs at 50° C. The dried granules are sized next with a 20 mesh screen. Then, a lubricant is passed through an 80 mesh screen and added to the granulation. The granulation is then put into milling jars and mixed on a jar mill for 15 minutes.

The composition forming blend is then compressed using a Manesty ® tablet press. In one manufacture, a 4-station press can be used. The speed of the press is set, for example, at 30 rpm and the maximum load set at 1-2 tons. The dosage forms are tableted using a standard concave punch, a standard round punch, or the like.

The dosage form of the invention can be manufactured also by other standard techniques. For example, in one manufacture, the beneficial drug and other ingredients comprising the compartment are blended and pressed into a solid mass. The solid mass possesses dimensions that correspond to the internal dimensions of the area the mass is to occupy in the dosage form. The drug and other ingredients can be blended also with a solvent and mixed into a solid, or semisolid form by conventional methods such as ballmilling, calendering, stirring, or rollmilling and then pressed into a preselected shape. The pressed shape then is surrounded with the exterior wall, and with the outermost coat.

Another manufacturing process that can be used for providing the compartment forming composition comprises blending the powdered ingredients in a fluid bed granulator. After the powdered ingredients are dry blended in the granulator, a granulating fluid, for example a binder in water, is sprayed onto the powders. This process granulates all the ingredients present therein while adding the granulating fluid. The coated powders then are dried in the granulator. After the granules are dried, a lubricant is added to the granulator. The granules then are pressed in the manner described above.

A number of dosage forms for dispensing chlorpheniramine were prepared according to the following procedure. First, 12 mg of chlorpheniramine maleate and 51.3 mg of mannitol were individually passed through a 40 mesh screen and then mixed in a blender for about 15 minutes. Next, 2.7 mg of Povidone ® poly(vinylpyrrolidone) is dissolved in distilled water and then added to the mixing blender and the ingredients blended for about 15 minutes to assure a thorough blend. The poly(vinyl-pyrrolidone) solution was added slowly to the blend until granulation was obtained as evidenced by the resultant wet granulation. The wet granulation was dried overnight and sized through a 10 mesh screen. The dry granules were mixed with 0.8 mg of magnesium stearate, which magnesium stearate was previously screened through an 80 mesh screen, and all the ingredients blended for 5 minutes to yield a homogeneous blend.

Next, the above prepared chlorpheniramine maleate blend was added to Manesty ® press, and using a 7/32 inch punch and die the blend was pressed under a pressure of 1 ton. The pressed ingredients weighed 67 mg.

Then, compressed chlorpheniramine maleate compressed composition was surrounded with a wall. The wall was formed from a composition comprising 75 wt. % cellulose triacetate having an acetyl content of 43.5%; 25 wt. % hydroxypropyl cellulose in a cosolvent comprising 80% methylene chloride and 20% methanol to yield a wall forming composition comprising 3% solids. The wall forming composition was prepared by mixing the two solvents and slowly adding the cellulose triacetate and the hydroxypropyl cellulose until all the solids dissolved in the cosolvent. The compressed composition was placed in an Aeromatic ® coater and coated at 40° C. until surrounded with a semipermeable wall about 3.4 mil (0.08 mm) thick. The wall weighed about 7.4 mg. The dosage form was dried in a forced air oven at 50° C. with 50% relative humidity for 2 days and then transferred to a 50° C. forced air oven for 5 days. The dry dosage form was drilled on two distant surfaces to produce on each surface a 10 mil (0.256 mm) passageway. The dosage form had an average rate of release of about 1 mg/hr over a 12 to 14 hr release period.

Another dosage form was prepared in the manner described immediately above with all the conditions as set forth, except that the dosage form of this example comprised a chlorpheniramine maleate outermost overcoat. The overcoat comprised 80 wt. % chlorpheniramine maleate and 20 wt. % hydroxypropyl cellulose. The overcoat was formed by dissolving the chlorpheniramine maleate in water and then adding the hydroxypropyl cellulose until all the solids dissolved in the aqueous solution. The overcoat was applied to the exterior surface of wall in an Aeromatic ® Hi-Coater. The coated dosage form was dried in an oven at 50° C. for 4 days. The dried overcoat composition comprised 4 mg of chlorpheniramine maleate.

The following additional dosage forms were prepared according to the mode and the manner described immediately above: (a) a dosage form comprising 12 mg of chlorpheniramine maleate, 65.5 mg of mannitol, 1.6 mg of polyvinylpyrrolidone, 0.8 mg of magnesium stearate and 9 mg of microcrystalline cellulose, with a wall comprising 75 wt. % cellulose triacetate having an acetyl content of 43.5% and 25 wt. % hydroxypropyl cellulose, with a pan of 10 mil passageways; (b) a dosage form comprising in its compartment 8 mg of chlorpheniramine maleate, 43.7 mg of mannitol, 1.1 mg of (polyvinylpyrrolidone) and 0.5 mg of magnesium stearate, with a wall surrounding the compartment comprising 75 wt. % cellulose triacetate having an acetyl content of 43.5% and 25 wt. % hydroxypropyl cellulose, a pan of ten mil passageways, and an exterior layer comprising 2.0 mg of chlorpheniramine maleate; (c) a dosage form as described (b) except that the exterior layer comprises 4 mg of chlorpheniramine maleate; and, (d) a dosage form as described in (b) or (c) with compartment also containing 4.5 mg of microcrystalline cellulose.

In summary, it will be appreciated that the present invention contributes to the delivery art an unobvious dosage form that possesses practical utility. While the invention has been described and pointed out in details with reference to operative embodiments thereof, it will be understood that those skilled in the art will appreciate that various changes, modifications, substitutions and omissions can be made without departing from the spirit of the invention. It is intended therefore, that the invention embraces those equivalents within the scope of the claims which follow.

We claim:

1. A dosage for for delivering chlorpheniramine to a biological environment of use, the dosage form comprising:
   (a) a wall comprising in at least a part a composition comprising a member selected from the group consisting of a cellulose acylate, a cellulose diacylate and a cellulose triacylate, which wall is permeable to the passage of an exterior fluid, substantially impermeable to the passage of chlorpheniramine, and surrounds and forms:
   (b) a compartment;
   (c) a composition in the compartment comprising a dosage unit amount of chlorpheniramine and mannitol, with the amount of mannitol and the amount of chlorpheniramine being selected to provide a mannitol concentration of from 1.5 to 6 times greater than the chlorpheniramine; and,
   (d) at least one passageway in the wall connecting the compartment with the exterior of the dosage form for dispensing chlorpheniramine at a substantially even rate to the environment of use over time.

2. The dosage form for delivering chlorpheniramine according to claim 1, wherein chlorpheniramine is present as a pharmaceutically acceptable salt.

3. The dosage form for delivering chlorpheniramine according to claim 1, wherein the composition comprises chlorpheniramine present as a pharmaceutically acceptable salt and mannitol.

4. The dosage form for delivering chlorpheniramine according to claim 1, wherein chlorpheniramine is present as chlorpheniramine meleate.

5. The dosage form for delivering chlorpheniramine according to claim 1, wherein the cellulose triacylate is cellulose triacetate.

6. The dosage form for delivering chlorpheniramine according to claim 1, wherein the compartment comprises from 2 to 24 mg of chlorpheniramine.

7. The dosage form for delivering chlorpheniramine according to claim 1, wherein the dosage form comprises an outermost layer comprising chlorpheniramine.

8. The dosage form for delivering chlorpheniramine according to claim 1, wherein the dosage form comprises an outermost layer comprising from 1 to 15 mg of chlorpheniramine.

9. The dosage form for delivering chlorpheniramine according to claim 1, wherein environment of use is the gastrointestinal tract, and the dosage form is adapted for oral admittance into said environment of use.

* * * * *